US008975444B2

(12) United States Patent
Purola et al.

(10) Patent No.: US 8,975,444 B2
(45) **Date of Patent: *Mar. 10, 2015**

(54) CUMENE OXIDATION

(75) Inventors: Veli-Matti Purola, Hamari (FI); Anja Mannerla, Espoo (FI)

(73) Assignee: Borealis AG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/140,042

(22) PCT Filed: Dec. 17, 2009

(86) PCT No.: PCT/EP2009/009122

§ 371 (c)(1), (2), (4) Date: Aug. 26, 2011

(87) PCT Pub. No.: WO2010/069586

PCT Pub. Date: Jun. 24, 2010

(65) Prior Publication Data

US 2011/0301384 A1 Dec. 8, 2011

(30) Foreign Application Priority Data

Dec. 17, 2008 (EP) .................................... 08171942

(51) Int. Cl.
*C07C 409/10* (2006.01)
*C07C 407/00* (2006.01)

(52) U.S. Cl.
CPC ............. *C07C 409/10* (2013.01); *C07C 407/00* (2013.01); *C07C 407/003* (2013.01)
USPC ............ 568/569; 568/385; 568/558; 568/571

(58) Field of Classification Search
CPC .............................. C07C 37/08; C07C 409/10
USPC ........... 568/570, 569, 385, 558, 571; 422/604
See application file for complete search history.

(56) References Cited

U.S. PATENT DOCUMENTS 5,908,962 A * 6/1999 Zakoshansky et al. ....... 568/571
6,225,513 B1 * 5/2001 Zakoshansky et al. ....... 568/798
6,465,695 B1 10/2002 Fulmer
7,312,365 B2 * 12/2007 Black ........................... 568/798
7,393,984 B1 * 7/2008 Zakoshansky et al. ....... 568/569
2009/0171126 A1 7/2009 Zakoshansky et al.

FOREIGN PATENT DOCUMENTS

EP 0816335 A1 1/1998
GB 1006319 A 9/1965
JP 4305564 A 10/1992
JP 2000290249 A 10/2000
JP 2000302752 A 10/2000
JP 2003231674 A 8/2003
WO WO2009080341 A1 7/2009

OTHER PUBLICATIONS

International Search Report and Written Opinion for Application No. PCT/EP2009/009121 dated Jun. 4, 2010.
Office Action for U.S. Appl. No. 13/139,932 dated Sep. 26, 2012.
International Search Report and Written Opinion for Application No. PCT/EP2009/009122 dated Mar. 29, 2010.
Office Action for U.S. Appl. No. 13/139,932 dated Apr. 17, 2013.
US Office Action, dated May 8, 2014 in U.S. Appl. No. 13/139,932.
Sunoco/UOP Phenol Process, UOP LLC, 2004.
Weber, Large Bubble Columns for the Oxidation of Cumene in Phenol Processes, Chem. Eng. Technol. 25(5):553-558, 2002.
Weber et al., Phenol, Wiley-VCH Verlag GmbH & Co. KGaA, Weinheim, pp. 1-17, 2005.

* cited by examiner

*Primary Examiner* — Fereydoun G Sajjadi
*Assistant Examiner* — Pancham Bakshi
(74) *Attorney, Agent, or Firm* — Meunier Carlin & Curfman, LLC

(57) ABSTRACT

A process for oxidizing cumene to cumene hydroperoxide using an oxygen containing gas, which process composes—conducting a cumene feed and an oxygen containing gas feed to at least the first oxidation reactor in a series of 3-8 reactors, thereby forming an oxidation mixture, and—conducting the oxidation mixture from one oxidation reactor to at least one subsequent reactor, wherein—the reactors are operated with reducing liquid levels; —the oxidation is operated as a dry oxidation, whereby the only gaseous feeds conducted to the oxidation reactors are the cumene feed and the oxygen containing gas feed; —the oxygen containing gas feed is washed with caustic and then with water to remove all acidic or caustic traces before conducting it into an oxidation reactor; —the pressure within each oxidation reactor is in the range of 0-10 barg; —the off-gases from the top section of each oxidation reactor are separated and cooled, whereby a condensate containing unreacted cumene is formed, and—washing the condensate and recycling at least a part of it to at least the first oxidation reactor; —the non-condensed off-gases are treated in a thermal oxidizer; and—the first reactor in the series of oxidation reactors has a liquid inventory of 30-300% larger than in the remaining reactors, preferably 50-100%, or the first two reactors in the series of oxidation reactors have a liquid inventory of 30-300% larger than in the remaining reactors, preferably 50-100%.

20 Claims, 1 Drawing Sheet

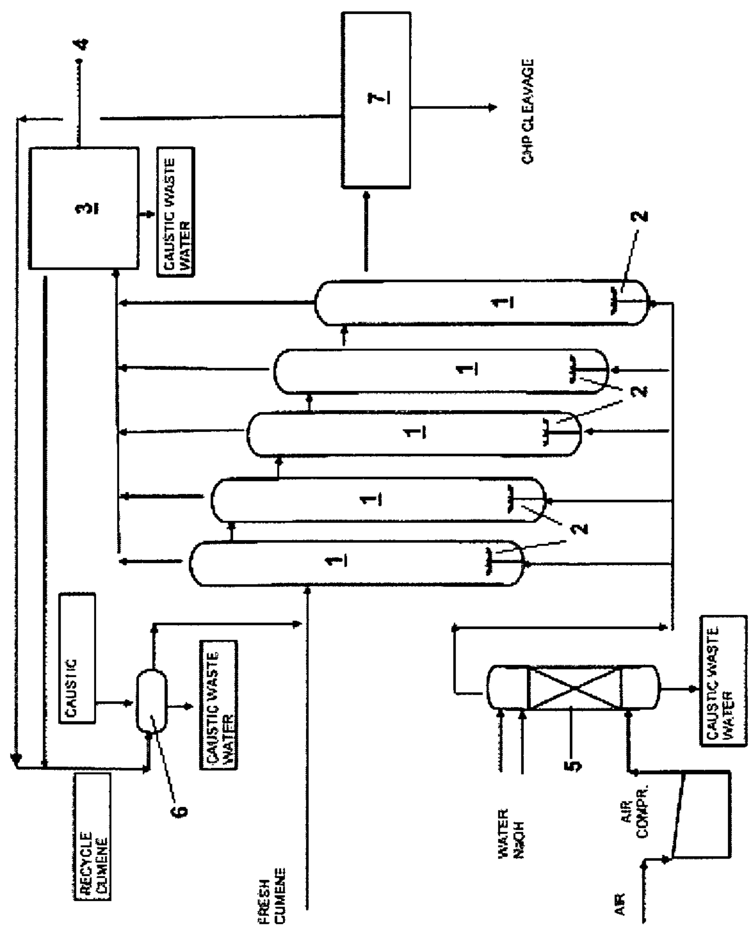
4
7
CHP CLEAVAGE
3
CAUSTIC WASTE WATER
2
1
CAUSTIC
CAUSTIC WASTE WATER
RECYCLE CUMENE
6
FRESH CUMENE
WATER
NaOH
5
CAUSTIC WASTE WATER
AIR COMPR.
AIR

CUMENE OXIDATION

CROSS REFERENCE TO RELATED APPLICATIONS

This application is a 35 USC 371 national phase of International Application No. PCT/EP2009/009122 filed Dec. 17, 2009, which claims priority to European Patent Application No. 08171942.9 filed Dec. 17, 2008, the contents of each are hereby incorporated herein by reference in their entirety.

BACKGROUND OF THE INVENTION

1. Field of the Invention

The present invention concerns a process for the oxidation of cumene to cumene hydroperoxide, wherein the selectivity has been improved.

2. Description of Related Art

Phenol is commonly manufactured through a cumene procedure, wherein cumene is oxidized to cumene hydroperoxide (CHP) and the resulting oxidation product mixture is concentrated and subjected to a cleavage reaction. Subsequently, the cleavage product mixture is conducted to a distillation section, wherein the main products of the cleavage reaction, i.e. phenol and acetone, are first separated and then purified through a series of distillation steps or other purification steps.

In the prior art, oxidation of cumene is generally carried out using a so-called wet-oxidation procedure, in which oxidation takes place in solution with the help of an aqueous solution of, for example, a carbonate. Dry oxidation procedures, where the only compounds introduced into the reaction mixture are the starting material (cumene) and the oxidation gas, are getting more common.

A disadvantage of the wet procedures is that they require, among others, a step of removing the carbonate and neutralizing the aqueous oxidized mixture, which has been rendered alkaline by the carbonate, before the oxidation product (CHP) can be concentrated.

The liquid phase oxidation of cumene is explained in terms of a radical mechanism by Kazua Hattori et al. in Journal of Chemical Engineering of Japan, vol. 3, no. 1, (1970), p. 72-78. The main side products formed in the oxidation are acetophenone and carbinol. The process is generally thought to follow the following scheme

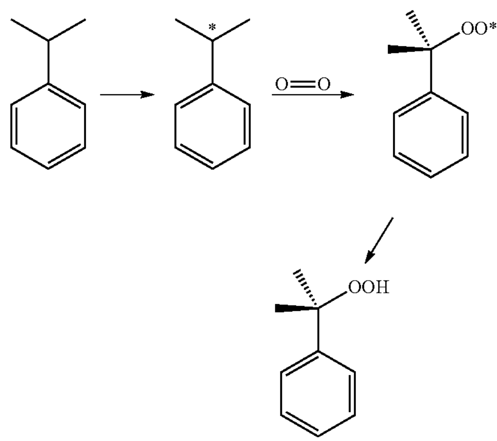

The formation of acetophenone (AcPh) is problematic, since it is not separated from the product mixture downstream from the oxidation. Carbinol (particularly dimethyl benzyl alcohol, DMBA) is partly recovered by converting it to α-methyl styrene (AMS) and by the subsequent hydrogenation of AMS to cumene. However, AMS as such is a source of heavy products, such as AMS dimers, which are not recovered downstream.

Cumene hydroperoxide selectivity is normally calculated on a molar basis from the cumene oxidation products:

CHP/(CHP+AcPh+DMBA+2DCP)

(DCP=dicumyl peroxide.) Typical values for the total selectivity in the oxidation are in the range of 92-94%.

Operation and design parameters of the oxidation, such as the pressure, the temperature, the CHP concentration, the residence time, the number of reactors, the treatment of the recycle streams, the treatment of the off-gas and cooling of the reactors, have an effect on the selectivity. Thus, the right selection of these parameters is important. It is also important that the feeds of cumene and, for example, air are properly treated to remove inhibitors, such as phenol, AMS, sulphur and carbon dioxide, or other impurities, such as inorganic acids or bases or free-radical generating compounds, since these impurities may cause the premature decomposition of the newly formed CHP. This premature decomposition may for example be caused by the impurities lowering the temperature at which the CHP decomposes. The presence of these impurities may also lead to a different, undesirable decomposition mechanism, thus leading to the formation of other impurities.

Oxidation of cumene into cumene hydroperoxide (CHP) has been thoroughly described in the prior art (as in GB 1006319, JP 4305564, JP 2000290249, JP 2000302752 and JP 2003231674), but there is still a need for further improving the process, since every change in a process parameter may have a significant effect on the others, thus causing a significant change for the product quality and quantity. For example, a decreased reaction rate may be compensated by an increase in the temperature, whereas a higher temperature causes an increase in the decomposition of CHP. Further, the CHP decomposition product, phenol, will cause a decrease in the reaction rate even in small concentrations, such as from a level of 10 ppm, e.g. a level of 10-100 ppm. Formation of acetophenone, on the other hand, will cause a decrease in the pH and an increase in the decomposition of phenol.

Improvements have been attempted in the prior art, for example, by positioning the oxidation reactors at reducing elevations, as in JP 2000290249, whereby the need for pumps or other similar means for moving the oxidation reaction mixture from one reactor to the next is removed, or by making the capacity of the oxidation reactors smaller one by one, as in JP 2000302752, whereby the reaction rate will be highest in the first reactor. In JP 2003231674, it has been attempted to optimize the oxidation reaction by limiting the velocity of the oxygen-containing gas bubbled through an oxidation reactor.

SUMMARY OF THE INVENTION

It is an aim of the present invention to provide an improved process for the oxidation of cumene.

Particularly, it is an aim of the present invention to provide an oxidation process, wherein process parameters are selected to give a higher selectivity towards CHP compared to the prior art.

Thus, viewed from one aspect the invention provides a process for oxidizing cumene to cumene hydroperoxide using an oxygen containing gas, which process comprises

- conducting a cumene feed and an oxygen containing gas feed to at least the first oxidation reactor in a series of 3-8 reactors, thereby forming an oxidation mixture, and
- conducting the oxidation mixture from one oxidation reactor to at least one subsequent reactor in the series, wherein

- the reactors are operated with reducing liquid levels;
- the oxidation is operated as a dry oxidation, whereby the only feeds conducted to the oxidation reactors are the cumene feed and the oxygen containing gas feed,
- the pressure within each oxidation reactor is in the range of 0-10 barg,
- the off-gases from the top section of each oxidation reactor are separated and cooled, whereby a condensate containing unreacted cumene is formed;
- the condensate is washed and at least a part of it is recycled to at least the first oxidation reactor;
- the non-condensed off-gases are treated in a thermal oxidizer; and
- the first reactor in the series of oxidation reactors has a liquid inventory of 30-300% larger than in the remaining reactors, preferably 50-100%, or the first two reactors in the series of oxidation reactors have a liquid inventory of 30-300% larger than in the remaining reactors, preferably 50-100%.

In the present invention, selection of process parameters means selecting and determining the combination of parameters that gives the best possible selectivity in an oxidation process according to the present invention.

The present invention concerns a process for oxidizing cumene into cumene hydroperoxide using an oxygen containing gas such as air. The invention also concerns an apparatus suitable for said oxidation.

Considerable advantages are obtained by means of the invention. Thus, the present invention provides an oxidation process, wherein the total selectivity of the oxidation of cumene into CHP has been improved to more than 94%, preferably more than 94.5%.

Further, no carbon beds are necessary for treating the off-gases conducted from the oxidation reactors. These are required, e.g. in low-pressure oxidation procedures to prevent the loss of products or starting materials.

Next, the invention will be described more closely with reference to the attached drawings and the following detailed description.

BRIEF DESCRIPTION OF THE DRAWINGS

FIG. 1 depicts the process and the apparatus according to a preferred embodiment of the present invention, for oxidizing cumene to cumene hydroperoxide using air.

DETAILED DESCRIPTION OF THE INVENTION

The present invention concerns a process for oxidizing cumene to cumene hydroperoxide using an oxygen containing gas such as air. The oxygen containing gas feed is preferably air, e.g. industrial air. However, a more concentrated oxygen gas may be used. The oxygen content of the oxygen containing gas may be up to 100%, preferably about 22-80% oxygen. The other components of the oxygen containing gas feed should be inert gases, typically nitrogen. In a preferred embodiment, air is used without modification (i.e. without oxygen enrichment) other than the cleaning/purification procedures documented below.

No other gases need to be added to the reactors in the present invention and this forms a feature of the invention, i.e. that the only gaseous feed to the reactors in the invention is the oxygen containing gas.

The process of the invention comprises conducting cumene to at least the first reactor in the series. Typically this cumene feed is quite pure and essentially contains cumene and minor amounts of impurities. Preferably therefore, this feed is at least 95 wt % cumene, preferably at least 99 wt % cumene. It may contain recycled cumene as explained in further detail below or recycled cumene may be fed separately to the first (or other) reactors in the series. This cumene feed is preferably a liquid feed. Whilst this fresh cumene feed can be fed to more than one reactor in the series, it is especially preferred if fresh cumene (i.e. cumene not part of the oxidation mixture) is fed to the first reactor only.

Along with cumene, an oxygen containing gas is also feed to at least the first reactor in the series to thereby form an oxidation mixture. The cumene feed and oxygen containing gas feed are preferably fed separately.

Once the oxidation mixture is formed in the first reactor, CHP forms. That part of the oxidation mixture which is displaced by the liquid being fed into a reactor is then conducted from the first reactor to at least one subsequent reactor, preferably the next one in the series. It is within the scope of the invention however for the oxidation mixture to be split and fed to one or more subsequent reactors. It is also within the scope of the invention for some transfers to occur in series and some transfers to be split and fed to different reactors.

Thus reactors can be arranged in parallel or in series or a mixture thereof. Other than in the last reactor, oxidation mixture from a reactor should be transferred to at least one downstream reactor in the series. Oxidation mixture from each reactor is preferably transferred to at least the next reactor downstream thereof in the series.

The reactors in the process of the invention are preferably connected only in series so that the oxidation mixture passes from one reactor to the next one in the series. It will be appreciated that the process of the invention will run continuously so there will always be new feed material entering and reacted material leaving the reactor.

Thus, to each subsequent reactor in the series (i.e. not the first), material is preferably transferred from the previous reactor. Thus, a liquid feed comprising unreacted cumene, its oxidation product and impurities is preferably fed from reactor to reactor in the series as the oxidation mixture. Thus, whilst cumene is formally transferred to each reactor in the series, it is preferably only the first reactor that has a dedicated and preferably essentially pure cumene feed. To all other reactors, any cumene is preferably added only as an unreacted part of the transferring oxidation mixture and that is not considered a "cumene feed" herein.

It will be appreciated that the amount of cumene in the oxidation mixture will reduce as the oxidation mixture passes from reactor to reactor as more cumene is converted to CHP and more removed from the top gases. As the reaction progresses therefore, each transfer mixture preferably contains less cumene and more CHP than the previous transfer mixture.

An oxygen containing gas is also fed, preferably to the bottom section, of each oxidation reactor, in the series of 3-8 reactors, thereby maintaining an oxidation mixture in each reactor. Unlike cumene therefore, fresh oxygen containing gas is preferably added to every reactor in the series. The oxidation mixture feed and oxygen containing gas feed are preferably fed separately.

The final oxidation mixture can be collected from the last oxidation reactor in the series through an outlet.

The oxygen containing gas is washed before use. Ideally this is achieved using first a diluted caustic solution, e.g. a solution having a pH of 8-12, preferably 10-12, in order to remove all acidic traces, such as $SO_2$ and $CO_2$. Water can then be used in order to remove any caustic traces.

Typical residence time in the reactors is 1-4 hours.

The reactors are operated with reducing liquid levels, whereby the driving force for passing the oxidation mixture from one reactor to the next one is gravity. This minimizes the use of pumps which is economic in terms of energy consumption but also reduces the amount of heat present and hence CHP decomposition.

In the context of the present invention, the term "reducing liquid levels" means that the upper surface of the oxidation mixture gets lower in each oxidation reactor following the first one. The term is not intended to limit the way in which the reactors are positioned, although the reactors may be placed at reducing heights relative to the ground or relative to sea level. The term reducing liquid levels does not therefore mean less oxidation mixture is present, only that the upper surface of the oxidation mixture is lower relative to sea level than the previous oxidizer.

This may also be achieved by increasing the diameter of the reactor to increase volume and so on.

The number of reactors is 3-8, preferably 3-6, most preferably 5-6. As noted above, they are operated with reducing liquid levels, and preferably they are also placed at reducing elevations. Thus, the first reactor has the highest liquid level, and is preferably placed at the highest elevation, whereas the last one has the lowest liquid level, and is preferably placed at the lowest elevation (compared to the sea level). Thus, the liquid driving force is gravity and no pumps are required to drive the oxidation mixture from one reactor to the next. This results in a minimized residence time of the oxidation mixture in the reactors, and no heat input from any pumps affect the operating conditions.

The oxidation is operated as a dry oxidation, i.e. no aqueous phase containing alkaline component such as sodium carbonate is separately added to the oxidation reactors.

The reactors are all preferably operated at a pressure of 0-10 barg. According to a preferred embodiment, the oxidation is operated at a pressure above atmospheric pressure, e.g. 1.0 to 8.0 barg, preferably at a pressure of 2.0-8.0 barg, more preferably 2.5-6.0 barg, most preferably 3.0-4.5 barg. A pressure lower than atmospheric pressure could result in a loss of some unoxidized cumene with the off-gases to the thermal oxidizer. These pressures are present therefore in every reactor in the series.

It will be appreciated however that there is no requirement to operate all reactors at the same pressure. Optionally, a higher pressure may be used in the first reactor than in the following ones. Thus, the first reactor could be operated at a pressure of 4.5-5.5 barg, while the following reactors could be operated at a pressure of 3.5-4.5 barg.

In one embodiment, the first of the reactors has a larger liquid inventory than the other ones, with a difference of 30-300% more than the regular inventory, preferably with a difference of 50-100%. This is due to the low concentration of CHP in the first reactor, which could take advantage of a larger inventory. The oxidation reaction has a higher selectivity at lower CHP concentrations due to fewer side reactions involving CHP. By using a larger first reactor (and optionally second) reactor more CHP is produced at a higher selectivity and the residence time can be kept lower in the subsequent reactors where more side reactions take place.

According to another preferred embodiment, the first two of the reactors have a larger liquid inventory than the other ones, with a difference of 30-300% more than the regular inventory (i.e. the average of the other reactors), preferably with a difference of 50-100%.

It is preferred therefore if the first or the first two reactors in the series are larger than the other reactors. It is preferred if the reactors with the larger inventories are approximately same size. The reactors with lower liquid inventories are preferably all substantially same size.

The temperature generally decreases when going downstream from the first reactor. Thus, the first reactor is operated at the highest temperature and the last reactor is operated at the lowest temperature. The operating temperature is 90-115° C., preferably 95-110° C. Since the oxidation is an exothermic reaction, the reactors following the first one may require external cooling, while the first reactor may require heating to the required temperature level, which may take place for example by heating the cumene feed or by heating the circulating streams with steam.

According to a preferred embodiment, the operating temperature is 95-115° C. when the number of reactors is six, whereas it is 96-110° C. when the number of reactors is three.

According to the present invention, the concentration of CHP at the outlet of the last oxidation reactor is 22-32%, preferably 24-28%.

Off gases from each reactor are separated from the oxidation mixture at the top of each reactor. The off-gases are typically combined and cooled, whereby a condensate containing unreacted cumene is formed. This condensate can be washed and recycled, while the non-condensed off-gases are treated, for example in a thermal oxidizer. The thermal oxidizer decomposes any hazardous gases at a high temperature to allow their release into the atmosphere.

The cumene left unoxidized after passing the last oxidation reactor is separated from the CHP. Ideally some or all of the separated cumene is recycled to be used as a cumene feed for the oxidation reaction. The recycled cumene is typically washed before returning to the reactors. This recycled cumene is preferably washed using first a caustic (i.e. basic) solution, preferably containing 0.2 to 2.0 wt % of NaOH, more preferably about 0.5 wt % of NaOH wt %, in order to purify it from acids, phenol and methanol, and then water in order to purify it from caustic traces.

Likewise the condensates formed from the off-gases are combined and washed using first a caustic solution, preferably containing 0.2 to 2.0 wt % of NaOH, more preferably about 0.5 wt % of NaOH, in order to purify them from contaminants comprising acids, phenol and methanol, and subsequently using water, in order to purify them from excess caustic, phenol and methanol. These washing processes are most preferably carried out as described in European patent application no. 07150215.

Recycled cumene can be fed back into the first reactor (all reactors or some reactors etc) along with fresh cumene or simply as a feed containing only recycled cumene. Thus, there can be a separate cumene recycle feed or the recycled cumene can be mixed with the main cumene feed. The latter is preferable.

The apparatus of the present invention preferably contains the following parts (FIG. 1)

1 oxidizing reactors
2 air spargers
3 condensers
4 thermal oxidizer
5 two-stage air scrubber
6 cumene purification unit
7 concentrator The apparatus thus contains a series of 3-8 oxidizing reactors 1, which are operated with reducing liquid levels so that the first reactor has the highest liquid level and the last one has the lowest liquid level, whereby the liquid driving force for passing the oxidation mixture from one reactor to the next is gravity, an air sparger 2 in each reactor 1 for evenly distributing the air conducted into the reactor 1, internal cooling coils for cooling the oxidation mixture (not shown in FIG. 1), one or more condensers 3 connected to the top section of the reactors 1, for condensing the off-gases, and a thermal oxidizer 4 connected to the condenser(s) 3 for treating the non-condensed off-gases. There may be provided a separate condenser 3 for each oxidation reactor 1, but preferably the off-gases are combined, and subsequently conducted to one single condenser 3 for combined condensing.

According to a preferred embodiment of the present invention, the apparatus further comprises a two-stage air scrubber 5 for purifying the oxygen containing gas, e.g. air, to be conducted into the reactors 1, as well as a cumene purification unit 6 for purifying the cumene starting material.

After the reaction mixture has been conducted through the oxidation reactors 1, it is conducted to a concentrator 7 for removing unreacted cumene and some by-products and impurities and, thus, concentrating the CHP of the mixture. Also at this stage, the liquid driving force for passing the mixture to the concentrator 7 is gravity, whereby no pumps are needed.

The concentration is preferably carried out using a concentrator that preferably functions in 2-3 stages of distillation, more preferably 3 stages. The main goal of the concentration is to remove unreacted cumene from the reaction mixture. The first distillation stage may be either a flash evaporation or a distillation with reflux, preferably a flash evaporation. The following stage(s) is (are) distillation stage(s) with reflux. The last distillation stage functions with the smallest burden, since the largest portion of cumene is removed in the first stage(s). The removed unreacted cumene is preferably condensed and washed as described above, and finally recycled to the oxidation step.

The cumene left unoxidized after passing the last oxidation reactor is separated from the CHP. Ideally some or all of the separated cumene is recycled from concentrator (7) to be used as a cumene feed for the oxidation reaction. The recycled cumene can be washed with a caustic wash and water as hereinbefore described.

The apparatus used to carry out the process of the invention forms a further aspect of the invention.

Thus, viewed from another aspect the invention provides an apparatus for oxidizing cumene to cumene hydroperoxide using an oxygen containing gas, comprising

- a series of 3-8 oxidizing reactors (1), which contain reducing liquid levels of oxidation mixture achieved by fixing the height of each reactor relative to sea level so that the first reactor is highest and each subsequent reactor is lower than the previous reactor, and
- a sparger (2) in each reactor (1) for distributing the gas conducted into the reactor (1),
- one or more condenser(s) (3) connected to the top section of the reactors (1), for condensing the off-gases;
- a thermal oxidizer (4) connected to the condenser(s) (3) for treating the non-condensed off-gases; and
- the first reactor in the series of oxidation reactors has a liquid inventory of 30-300% larger than in the remaining reactors, preferably 50-100%, or the first two reactors in the series of oxidation reactors have a liquid inventory of 30-300% larger than in the remaining reactors, preferably 50-100%.

The oxidizing process and the apparatus of the present invention may be used for oxidizing any organic compound with air into its hydroperoxide. Preferably, the apparatus is arranged in a phenol production process. The phenol production process typically comprises process steps, wherein phenol and acetone are produced through the oxidation of cumene to cumene hydroperoxide (CHP) and, subsequently, wherein the CHP is concentrated and cleaved into phenol, acetone and other cleavage products, which products are washed and desalted, and finally wherein the acetone is separated from the phenol and both products are purified.

The concentration of the CHP formed during the oxidation is increased in a series of concentration steps. According to a preferred aspect of the invention, the concentrated CHP is further processed, e.g., by subjecting it to a cleavage process. According to this preferred aspect, the obtained cleavage product mixture is conducted further to the distillation section of the phenol production process. In the distillation section, the cleavage product mixture is distilled, first in order to separate a crude distillate, containing, for example, acetone, water, cumene, AMS, hydroxyacetone and mesityl oxide, from a crude base product, containing, for example, phenol, acetophenone, carbinol, mesityl oxide and heavy hydrocarbons, and further to separate impurities from the product phenol and the product acetone.

Off-gases are collected from the top section of every oxidizing reactor 1 and cooled in a condenser 3, whereafter the formed condensate is washed using a caustic solution and, subsequently, returned to the mentioned step of washing the recycled cumene. The non-condensed off-gases are treated in a thermal oxidizer 4.

The invention claimed is:

1. A process for oxidizing cumene to cumene hydroperoxide using an oxygen containing gas, the process comprising

- conducting a cumene feed and an oxygen containing gas feed to at least the first oxidation reactor in a series of 3-8 reactors, thereby forming an oxidation mixture, and
- conducting the oxidation mixture from the first oxidation reactor directly to at least one subsequent reactor whereby the driving force for conducting the oxidation mixture from the first reactor is gravity, wherein

- the reactors are operated with reducing liquid levels;
- the oxidation is operated as a dry oxidation, whereby the only gaseous feeds conducted to the oxidation reactors are the cumene feed and the oxygen containing gas feed;
- the oxygen containing gas feed is washed with caustic and then with water to remove all acidic or caustic traces before conducting it into an oxidation reactor;
- the pressure within each oxidation reactor is in the range of 0-10 barg;
- the off-gases from the top section of each oxidation reactor are separated and cooled, whereby a condensate containing unreacted cumene is formed, and
- washing the condensate and recycling at least a part of the unreacted cumene from condensate of off-gases to at least the first oxidation reactor;
- the non-condensed off-gases are treated in a thermal oxidizer; and
- the first reactor in the series of oxidation reactors has a liquid inventory of 30-300% larger than in the remaining reactors, or the first two reactors in the series of oxidation reactors have a liquid inventory of 30-300% larger than in the remaining reactors.

2. The process of claim 1 wherein the oxygen containing gas is distributed evenly into the cumene using a sparger.

3. The process of claim 1, wherein the oxygen containing gas is conducted into each oxidation reactor in a series of 3-6 reactors.

4. The process of claim 1, wherein cumene is fed only to the first reactor in the series.

5. The process of claim 1, wherein the oxidation mixture is transferred between reactors in series and the driving force for the transfer between the reactors is gravity.

6. The process of claim 1, wherein the oxidation is carried out at a pressure of 1.0-8.0 barg.

7. The process of claim 1, wherein the oxidation is carried out at a temperature of 90-115° C.

8. The process of claim 1, wherein an oxidation product mixture is separated from the oxidation mixture in the last reactor of the series of reactors through a product outlet, the product mixture having a cumene hydroperoxide concentration of 22-32%.

9. The process of claim 8, wherein the cumene hydroperoxide in the oxidation product is concentrated in more than one distillation stage, wherein unoxidized cumene is removed from the oxidized product, condensed and recycled to the cumene feed.

10. The process of claim 9, wherein the unreacted cumene from the condensates of the oxidation off-gases and the unreacted cumene recovered from the oxidation product are combined and washed using a caustic solution, and the caustic-washed combined unreacted cumene are washed using water before being recycled to the cumene feed.

11. The process of claim 1, wherein residence time of the oxidation mixture in the remaining reactors is lower compared to the larger inventory reactor(s).

12. The process of claim 1, wherein the first reactor is operated at the highest temperature and the last reactor is operated at the lowest temperature.

13. The process of claim 1, wherein the first reactor in the series of oxidation reactors has a liquid inventory of 50-100% larger than in the remaining reactors, or the first two reactors in the series of oxidation reactors have a liquid inventory of 50-100% larger than in the remaining reactors.

14. The process of claim 1, wherein the oxygen containing gas is conducted into each oxidation reactor in a series of 5-6 reactors.

15. The process of claim 1, wherein the oxidation is carried out at a pressure of 2.5-6.0 barg.

16. The process of claim 1, wherein the oxidation is carried out at a pressure of 3.0-4.5 barg.

17. The process of claim 1, wherein the oxidation is carried out at a temperature of 95-110° C.

18. The process of claim 1, wherein an oxidation product mixture is separated from the oxidation mixture in the last reactor of the series of reactors through a product outlet, the product mixture having a cumene hydroperoxide concentration of 24-28%.

19. The process of claim 17, wherein the cumene hydroperoxide in the oxidation product is concentrated in 3 stages of distillation, wherein unoxidized cumene is removed from the oxidized product, condensed and recycled to the cumene feed.

20. The process of claim 18, wherein the unreacted cumeme from the condensates of the oxidation off-gases and the unreacted cumene recovered from the oxidation product are combined and washed using a caustic solution containing about 0.2-2.0% of NaOH, and the caustic-washed combined unreacted cumene are washed using water before being recycled to the cumene feed.

* * * * *